US006797301B1

(12) United States Patent
Duvert et al.

(10) Patent No.: US 6,797,301 B1
(45) Date of Patent: Sep. 28, 2004

(54) FUNGICIDE COMPOSITIONS FOR PROTECTING FRUITS

(75) Inventors: Patrice Duvert, Lyons (FR); Richard Mercer, Ecully (FR)

(73) Assignee: Aventis Cropscience SA (FR)

( * ) Notice: Subject to any disclaimer, the term of this patent is extended or adjusted under 35 U.S.C. 154(b) by 0 days.

(21) Appl. No.: 09/913,416

(22) PCT Filed: Feb. 11, 2000

(86) PCT No.: PCT/FR00/00339

§ 371 (c)(1),
(2), (4) Date: Oct. 15, 2001

(87) PCT Pub. No.: WO00/47047

PCT Pub. Date: Aug. 17, 2000

(30) Foreign Application Priority Data

Feb. 12, 1999 (FR) .............................. 99 01887

(51) Int. Cl.$^7$ .................. A01N 43/50; A01N 57/12; A01N 61/00
(52) U.S. Cl. .................. 426/333; 426/335; 426/616; 426/532; 504/127; 504/148
(58) Field of Search ................ 426/333, 335, 426/616, 532; 504/127, 148

(56) References Cited

U.S. PATENT DOCUMENTS

| | | | | |
|---|---|---|---|---|
| 3,950,559 A | * | 4/1976 | Kapoor et al. | 426/335 |
| 4,842,880 A | * | 6/1989 | Creason et al. | 426/303 |
| 4,990,351 A | * | 2/1991 | Orman et al. | 426/333 |
| 5,503,859 A | * | 4/1996 | Creason et al. | 426/308 |
| 6,235,684 B1 | * | 5/2001 | Knauf-Beiter et al. | 504/127 |

FOREIGN PATENT DOCUMENTS

| | | | |
|---|---|---|---|
| EP | 0524496 | | 1/1993 |
| EP | 0531837 | | 3/1993 |
| FR | 2754424 | | 4/1998 |
| WO | WO 93/22921 | * | 11/1993 |
| WO | 96/03044 | | 2/1996 |
| WO | WO 98/33381 | * | 8/1998 |
| WO | 0045638 | | 8/2000 |

OTHER PUBLICATIONS

*The Pesticide Manual*; Tenth Edition; The Royal Society of Chemistry; pp. 580–581 and 972–973.

"The effect of some fungicide treatments and storage regimes on the postharvest diseases of citrus fruits"; S. Toker, et al.; *Turk. J. Agric. For.*; 20(1); 73–83; 1996; Abstract.

"Biology and control of Coniophora eremophila on lemon trees in Arizona"; D.M. Bigelow, et al.; *Plant Dis.*; 80, No. 8; 934–39; 1996; Abstract.

"Spread of Phytophthora rot on stored citrus and its prevention by fungicide dips"; A Chitzanidis, et al.; *Bulletin OEPP*; 1990; vol. 20, No. 1; pp. 163–168; Abstract.

"Fenpropimorph: A promising fungicide for postharvest diseases in citrus fruits"; E. Cohen, et al.; *Phytoparasitica*, 18, No. 1, 17–26, 1990; Abstract.

*The Pesticide Manual*; Tenth Edition; The Royal Society of Chemistry; pp. 794–795.

"Differential Sensivity to Thiabendazole by Strains of Penicillium Italicum and P. Digitatum", Paul R. Harding, Jr., *Plant Disease Reporter*, vol. 56, No. 3 Mar. 1972, pp. 256–260.

"Penicillium Digitatum Biotypes with Reduced Sensitivity to Imazalil", *Phytopathology*, J.W. Eckert, 77(12), 1987, p. 1728.

* cited by examiner

*Primary Examiner*—N. Bhat
(74) *Attorney, Agent, or Firm*—Ostrolenk, Faber, Gerb & Soffen, LLP

(57) ABSTRACT

A fungicide composition useful for fighting against phytopathogenic fungi infesting or cable of infesting fruits contains a) at least a fungicide compound inhibiting mitochondrail respiration and b) at least a fungicide compound inhibiting sterol biosynthesis. A method of using the phytopathogenic fungicide for treating fruits against fungal disease is provided.

21 Claims, No Drawings

FUNGICIDE COMPOSITIONS FOR PROTECTING FRUITS

This application is a 371 of PCT/FR00/00339, filed Feb. 11, 2000.

The present invention relates to novel fungicide compositions useful in the treatment of fruits against fungal diseases, and the methods for treating fruits against fungal diseases using the said compositions.

It is well known that fruits, after they have been harvested, become covered with moulds, which causes them to rot.

These moulds appear after a long or shorter period, depending on the nature of the fruit or of the vegetable and the environmental conditions, and are the result of the development of one or more phytopathogenic fungi. These fungi, for the majority, and their mode of development are well known.

Thus, numerous methods for treating fruits have already been known and described.

Among them, there may be mentioned the application by immersion and/or brushing of the fruits after harvest in known fungicide solutions. Reference may be made, for example, to the work by A. Chitzanidis et al., *Bulletin OEPP*, 20(1), (1990), 163–168 or to that by E. Cohen et al., *Phytoparasitica*, 18(1), (1990), 17–26.

Other methods recommend a first treatment by spraying fungicide compounds on fruit trees, and then applying to the fruits other fungicides by immersion and/or brushing. This type of treatment is described in particular by S. Toker et al., *Turk. J. Agric. For.*, 20(1), (1996), 78-83.

Among the fungicides most commonly used for the treatment of fruits after harvest, there may be mentioned imazalil (described in "The Pesticide Manual", 10th edition, British Crop Protection Council, page 580), thiabendazole (ibid. page 972) or SOPP (sodium o-phenylphenate, ibid. page 794), which have so far proved the most effective.

These compounds are indeed particularly active against strains of Penicillium, which are responsible for numerous fungal diseases.

Unfortunately, strains of Penicillium resistant to thiabendazole (P. R. Harding Jr., *Plant Dis. Rep.*, 56(3), (1972), 256–260), and more recently resistant to imazalil have appeared (see for example the publications by J. W. Eckert, *Phytopathology*, 77(12), (1987), 1728, and *ISPP Chemical Control Newsletter*, 10, (1988), 36–38).

These compounds are moreover weakly active, or even inactive on other phytopathogenic fungi. In addition, while imazalil may be used for preventive and curative treatment, this curative effect remains limited over time.

It is also always desirable to improve the fungicide products used for treating fruits.

It is also always desirable to reduce the doses of chemical products applied to fruits, in particular by reducing the doses for application of the products.

It is finally always desirable to increase the range of antifungal products available so as to find among them those best suited to specific uses.

A first object of the present invention consists in providing fungicide compositions exhibiting a broad activity spectrum, that is to say possessing substantial activity on a number of phytopathogenic fungi greater than the number of phytopathogenic fungi treated with known compositions.

A second object of the invention consists in providing fungicide compositions possessing both a preventive effect and a curative effect, in particular an improved curative effect compared with the fungicide compositions currently used.

Another object of the present invention consists in providing fungicide compositions which are able to effectively control the strains of fungi resistant to known fungicide compositions.

Another aim of the present invention is to provide fungicide compositions which are effective at substantially lower doses compared with the doses currently applied.

Another object of the present invention consists in providing fungicide compositions applied to fruits so as to prevent or delay their rotting, while remaining suitable for consumption.

Other objects of the invention will appear in the disclosure of the invention which is presented in the remainder of the present description.

Surprisingly, it has been discovered that all these objects are achieved fully or partially by virtue of the fungicide compositions which are the subject of the present invention.

The present invention therefore relates to fungicide compositions useful for controlling phytopathogenic fungi infesting or capable of infesting fruits, characterized in that they contain:
- at least one fungicide compound inhibiting mitochondrial respiration, and
- at least one fungicide compound inhibiting sterol biosynthesis.

Among the fungicide compounds inhibiting mitochondrial respiration there may be mentioned, for example, strobilurin and analogous compounds or derivatives, such as for example azoxystrobin, kresoxim-methyl, trifloxystrobin, picoxystrobin, discostrobin, but also 4-chloro-2-cyano-N,N-dimethyl-5-p-tolylimidazole-1-sulphonamide, 5-methyl-5-(4-phenoxyphenyl)-3-(phenylamino)-2,4-oxazolidine-dione (or famoxadone) as well as the compounds of general formula (I):

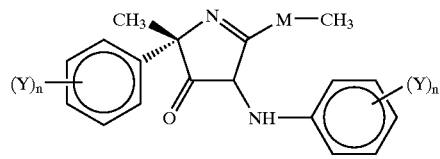

in which:
M represents an oxygen or sulphur atom;
n is an integer equal to 0 or 1;
Y is a fluorine or chlorine atom, or a methyl radical.

The compounds of formula (I) are known, in particular by patent application EP-A-0 629 616.

Preferably, there will be chosen from the compounds of formula (I) the compound for which M represents a sulphur atom and n is equal to 0, that is to say (4-S)-4-methyl-2-methylthio-4-phenyl-1-phenylamino-2-imidazoline-5-one, called Fenamidone.

The list of fungicide compounds inhibiting mitochondrial respiration should not be considered as being limiting, but as illustrating, for persons skilled in the art, the range of compounds inhibiting mitochondrial respiration available to them.

Likewise, by way of illustration, among the compounds inhibiting sterol biosynthesis which may be used in the fungicide compositions of the present invention, there may be mentioned, for example, imazalil.

Preferably, there will be chosen, for the fungicide compositions which are the subject of the invention, as inhibitor of mitochondrial respiration, a compound of formula (I) or famoxadone, and as inhibitor of sterol biosynthesis, imazalil.

Most preferably, the fungicide compositions according to the present invention comprise imazalil in combination with fenamidone.

The compositions according to the present invention are provided in the form of liquids which are viscous to a greater or lesser degree, ranging from a viscosity similar to that of water or of oil, to wax-type formulations.

As a general rule, the doses of fungicide compounds present in the compositions of the invention depend on the nature of the compounds themselves, the nature of the fruits to be treated and the nature of the diseases to be treated and their degree of infestation.

The doses of inhibitors of mitochondrial respiration used for the fungicide compositions of the present invention are advantageously between 10 mg/l and 1000 mg/l, preferably between 20 mg/l and 300 mg/l, preferably still between 40 mg/l and 150 mg/l, for example between 50 mg/l and 100 mg/l.

The doses of inhibitors of sterol biosynthesis used for the fungicide compositions of the present invention are advantageously between 100 mg/l and 3000 mg/l, preferably between 50 mg/l and 2500 mg/l, preferably still between 200 mg/l and 2000 mg/l, for example between about 400 mg/l and 1000 mg/l.

It is clearly understood that the fungicide compositions according to the present invention may contain, in addition to one or more inhibitors of mitochondrial respiration and one or more inhibitors of sterol biosynthesis, one or more other fungicide compounds known to persons skilled in the art and suitable for treating fungal diseases of fruits.

By way of nonlimiting example, the other fungicide compounds which may be included in the compositions of the invention comprise phosphorous acid, as well as its derivatives and its salts. A product which is most particularly suitable for the compositions of the present invention is the aluminium salt of phosphorous acid, called Fosetyl-Al (described in "The Pesticide Manual", 10th edition, British Crop Protection Council, page 530).

Thus, a most particularly preferred composition of the present invention comprises imazalil, fenamidone and fosetyl-Al.

The doses of these other fungicide compounds which may be added to the compositions according to the present invention depend on the types of diseases to be treated, their degree of infestation, the nature of the fruits to be treated and the actual nature of these compounds. Persons skilled in the art will know how to assess the doses to be applied which may be for example between 500 mg/l and 6000 mg/l, for example between 2000 mg/l and 4000 mg/l.

When fosetyl-Al is used, the dose for use is generally between 1000 mg/l and 1500 mg/l, preferably about 1200 mg/l.

It has therefore been discovered, surprisingly, that the addition of an inhibitor of mitochondrial respiration to an inhibitor of sterol biosynthesis substantially increases the activity spectrum of the fungicide compositions and possesses in particular an unexpected efficacy on the strains of phytopathogenic fungi resistant to the inhibitors of sterol biosynthesis.

Thus, the fungicide compositions according to the invention are effective for treating the majority of phytopathogenic fungi infesting or capable of infesting fruits, and in particular:

Phytophthora spp., for example brown rot of citrus fruits (*Phytophthora parasitica*), and gummosis of citrus (*Phytophthora citrophthora*);

Penicillium spp., for example blue mould (*Penicillium italicum*), and green mould (*Penicillium digitatum*);

bitter rot of citrus fruits (*Geotrichum candidum*);

black rot of citrus fruits (*Alternaria citri*);

anthracnose (*Colleotrichum gloeos-porioides*);

melanose or phomopsis rot (*Diplodia natalensis* or *Phomopsis citri*).

Other phytopathogenic fungi may also be controlled using the fungicide compositions of the invention. The nature of these other fungi partly depends on the nature of the other fungicides present in the compositions which are the subject of the invention.

The fruits which may be treated with the compositions according to the invention are of any type, and particularly those which may be damaged by the appearance of phytopathogenic fungi which are described above, in particular during prolonged storage of the said fruits.

Furthermore, the compositions according to the invention find a particularly advantageous use in the treatment of fruits after harvest, in order to prevent or delay their rotting, while remaining fit for consumption.

Thus, among the fruits which may be treated with the fungicide compositions of the invention, there may be mentioned in particular citrus fruits, for example lemons, oranges, grapefruits, citron fruit, clementines, mandarins, and the like.

It thus appears that the field of application of the fungicide compositions described here is not limited, and that these compositions may be used in all types of cases where protection or action against fungal attacks is needed in order to prevent or stop the rotting of edible fruits.

The compositions according to the invention comprise, in addition to the fungicide compounds described above, solid or liquid carriers which are acceptable in the fungal treatment of fruits and/or surfactants which are also acceptable in the fungal treatment of fruits. In particular, there may be used inert and customary carriers and customary surfactants. These compositions cover not only compositions ready to be applied to the fruits to be treated by immersion or using a suitable device, but also the commercial concentrated compositions which have to be diluted before application to the fruits.

These fungicide compositions according to the invention may also contain any sort of other ingredients such as, for example, protective colloids, adhesives, thickeners, thixotropic agents, penetrating agents, stabilizers, sequestrants, texturing agents, flavouring agents, taste enhancers, sugars, sweeteners, colorants and the like. More generally, the active substances may be combined with any solid or liquid additives corresponding to the usual formulation techniques.

In general, the compositions according to the invention usually contain from 0.05 to 95% (by weight) of active substance (the expression active substance is understood here to mean all the fungicide compounds contained in the present formulation), one or more solid or liquid carriers and, optionally, one or more surfactants.

The term "carrier", in the present disclosure, denotes a natural or synthetic organic or inorganic substance with which the active substance is combined to facilitate its application to fruits. This carrier is therefore generally inert and should be acceptable in the agri-foodstuffs sector. The carrier may be solid (clays, natural or synthetic silicates, silica, resins, waxes, solid fertilizers, and the like) or liquid (water, alcohols, in particular butanol, and the like).

The surfactant may be an emulsifying agent, a dispersing agent or a wetting agent of the ionic or nonionic type or a mixture of such surfactants. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols (in particular alkylphenols or arylphenols), salts of esters of sulphosuccinic acids, derivatives of taurine (in particular alkyl taurates), phosphoric esters of polyoxyethylated phenols or alcohols, esters of fatty acids and polyols, sulphate, sulphonate and phosphate functional group-containing derivatives of the above compounds. The presence of at least one surfactant is generally essential when the active substance and/or the inert carrier are not soluble in water and when the vector agent for application is water.

Accordingly, the compositions according to the invention may contain the active substance in very broad limits, ranging from 0.05% to 95% (by weight). Their content of surfactant is advantageously between 0.5% and 40% by weight. Unless otherwise stated, the percentages given in this description are percentages by weight.

These compositions according to the invention are themselves in fairly diverse, solid or liquid, forms.

As solid composition forms, there may be mentioned dustable powders (content of active substance which may be up to 100%) and granules, in particular those obtained by extrusion, by compacting, by impregnation of a granulated carrier, by granulation using a powder as starting material (the content of active substance in these granules being between 0.5 and 80% for these latter cases). Such solid compositions may be optionally used in the form of a liquid which is viscous to a greater or lesser degree, depending on the type of application desired, for example by diluting in water.

As liquid composition forms or forms intended to constitute liquid compositions during application, there may be mentioned solutions, in particular water-soluble concentrates, emulsions, suspension concentrates, wettable powders (or spraying powder), oils and waxes.

The suspension concentrates, which can be applied by spraying, are prepared so as to obtain a stable fluid product which does not form a deposit and they usually contain from 10 to 75% of active substance, from 0.5 to 15% of surfactants, from 0.1 to 10% of thixotropic agents, from 0 to 10% of appropriate additives, such as antifoams, corrosion inhibitors, stabilizers, penetrating agents and adhesives and, as carrier, water or an organic liquid in which the active substance is not or not very soluble: some organic solids or inorganic salts may be dissolved in the carrier to help prevent sedimentation or as antigels for water.

By way of example, here is a suspension concentrate composition:

EXAMPLE SC 1

| | |
|---|---|
| active substance | 500 g |
| polyethoxylated tristyrylphenol phosphate | 50 g |
| polyethoxylated alkylphenol | 50 g |
| sodium polycarboxylate | 20 g |
| ethylene glycol | 50 g |
| organopolysiloxane oil (antifoam) | 1 g |
| polysaccharide | 1.5 g |
| water | 316.5 g |

The wettable powders (or spraying powder) are usually prepared so that they contain 20 to 95% of active substance, and they usually contain, in addition to the solid carrier, from 0 to 30% of a wetting agent, from 3 to 20% of a dispersing agent, and, when necessary, from 0.1 to 10% of one or more stabilizers and/or other additives, such as penetrating agents, adhesives, or anticaking agents, colorants, and the like.

To obtain the spraying powders or wettable powders, the active substances are intimately mixed in appropriate mixers with the additional substances and ground with mills or other appropriate grinders. Spraying powders are thereby obtained whose wettability and suspendability are advantageous; they can be suspended with water at any desired concentration and these suspensions can be very advantageously used in particular for application, for example, to the leaves of plants or to seeds.

By way of example, here is a wettable powder (or spraying powder) composition:

EXAMPLE WP 1

| | |
|---|---|
| active substance | 50% |
| ethoxylated fatty alcohol (wetting agent) | 2.5% |
| ethoxylated phenylethylphenol (dispersing agent) | 5% |
| flour (inert carrier) | 42.5% |

The aqueous emulsions and dispersions, for example the compositions obtained by diluting a wettable powder according to the invention with water, are included in the general scope of the present invention. The emulsions may be of the water-in-oil or oil-in-water type and they may have a thick consistency such as that of a mayonnaise, or even a wax.

The fungicide compositions according to the invention may be formulated in the form of water-dispersible granules which are also included in the scope of the invention.

These dispersible granules, with an apparent density which is generally between about 0.3 and 0.6, have a particle size which is generally between about 150 and 2000 and preferably between 300 and 1500 microns.

The content of active substance in these granules is generally between about 1% and 90%, and preferably between 25% and 90%.

The remainder of the granule is essentially composed of a solid filler and optionally of surfactant adjuvants conferring on the granule properties of dispersibility in water. These granules may be essentially of two distinct types depending on whether the filler selected is soluble in water or otherwise. When the filler is water-soluble, it may be inorganic or, preferably, organic. In the case of an insoluble filler, it is preferably inorganic, such as for example kaolin or bentonite. It is in this case advantageously accompanied by surfactants (in an amount of 0.5 to 20% by weight of the granule) of which more than half, for example, consists of at least one essentially anionic dispersing agent such as an alkali or alkaline-earth metal polynaphthalenesulphonate or an alkali or alkaline-earth metal lignosulphonate, the remainder consisting of nonionic or anionic wetting agents such as an alkali or alkaline-earth metal alkylnaphthalenesulphonate.

Moreover, although not being essential, other adjuvants such as antifoams may be added.

The granule according to the invention may be prepared by mixing the necessary ingredients, followed by granulation based on several techniques known per se (pelletizer, fluidized bed, spray-dryer, extrusion and the like). The final step is generally crushing, followed by sieving to the particle size chosen within the abovementioned limits. It is also possible to use granules obtained as above and then impregnated with a composition containing the active substance.

Most advantageously, the compositions according to the present invention are suitable for application, to the fruits to be treated, by spraying, by immersion, by film-coating, by coating, and the like.

The present invention also relates to a method for treating fruits, characterized in that the fruits are treated with a fungicide composition according to the invention, by immersion, spraying, brushing, coating, film-coating, and the like. These treatment techniques are well known to persons skilled in the art.

By way of example, the treatment by immersion consists in directly immersing the fruits in an aqueous solution of a fungicide composition according to the invention. This operation may be carried out manually or mechanically.

A particularly preferred mechanical treatment is brushing, that is to say that the fungicide compounds are applied with brushes situated, for example, on top of rollers over which the fruits move.

Other techniques, such as spraying using apparatus provided with nozzles, or film-coating or coating, in drums or "concrete mixers" provided or otherwise with rollers, brushes and/or screw threads, involve known techniques which will not be presented in more detail here.

It should be noted that the treatment of fruits using the fungicide compositions according to the invention is preferably carried out after harvest, preventively and/or curatively, that is to say before and/or after a disease has appeared on the fruits treated.

The fungicide compounds contained in the compositions according to the invention may be applied to the fruits simultaneously, sequentially or separately.

Furthermore, the treatment with the fungicide compositions according to the invention is compatible with a conventional preharvest treatment, it being possible for this treatment to be of any known, fungicide and/or insecticide, type.

Such a fungicide and/or insecticide treatment combined with a treatment, preferably after harvest, with one or more fungicide compositions according to the present invention is also included in the scope of the present invention.

Finally, the present invention also relates to the fruits treated with one or more compositions according to the present invention.

The following examples are given without limitation with the sole aim of showing the excellent efficacy of the compositions according to the invention, and of showing how they are used.

Example 1 (curative action)

A small area of peel (of the order of 1 cm$^2$) was removed from lemons. After carrying out this operation, inoculation was carried out with a suspension of spores of *Penicillium digitatum* (concentration 3,900,000 spores/ml) at the rate of 5 drops per fruit at the site where the peel was removed. The lemons, at the rate of 3 fruits/test factor, were placed in cups, placed in bags and incubated at 20° C. for 24 hours. After this period, a fungicide treatment by spraying was carried out. The products and doses used were the following:

Reference composition A: fenamidone+fosetyl-Al at doses of 17+250, 33+500, 66+1000, 133 g+2000 mg of active substances per liter.

Reference composition B: imazalil (commercial formulation Deccosil Agrumes®, emulsifiable concentrate at 200 g/l) at the doses of 125, 250, 500 and 1000 mg of imazalil per liter.

Example of composition 1: Composition A+composition B at the doses of (17+250)+125, (33+500)+250, (66+1000)+500 and (133+2000)+1000 mg of active substances per liter (first batch of doses).

Example of composition 2: Composition A+Composition B at the doses of (10+150)+75, (20+300)+150, (40+600)+300 and (80+1200)+600 mg of active substances per liter (second batch of doses).

After the treatment, the lemons were again placed in bags and then placed again at 20° C. for 6 days.

On the 6th day after the treatment, scores were awarded. It consisted in determining the percentage of surface contaminated and, by comparing with a non-treated and inoculated control, defining the percentage efficacy.

Results

| Composition | Doses (mg/l) (fenamidone + fosetyl-Al + imazalil | % Efficacy |
|---|---|---|
| Composition A | (17 + 250) | 0 |
| | (33 + 500) | 16 |
| | (66 + 1000) | 0 |
| | (133 + 2000) | 0 |
| Composition B | 125 | 80 |
| | 250 | 32 |
| | 500 | 93 |
| | 1000 | 96 |
| Composition 1 (first batch of doses) | (17 + 250) + 125 | 52 |
| | (33 + 500) + 250 | 88 |
| | (66 + 1000) + 500 | 93 |
| | (133 + 2000) + 1000 | 98 |
| Composition 2 (second batch of doses) | (10 + 150) + 75 | 60 |
| | (20 + 300) + 150 | 88 |
| | (40 + 600) + 300 | 95 |
| | (80 + 1200) + 600 | 98 |

The untreated control is 83% contaminated.

Example 1 (preventive action)

The experimental protocal followed is identical to the one above apart from the fact that the treatment is this time carried out a day before the inoculation.

Results

| Composition | Doses (mg/l) (fenamidone + fosetyl-Al + imazalil | % Efficacy |
|---|---|---|
| Composition A | (17 + 250) | 0 |
| | (33 + 500) | 11 |
| | (66 + 1000) | 0 |
| | (133 + 2000) | 39 |
| Composition B | 125 | 67 |
| | 250 | 32 |
| | 500 | 93 |
| | 1000 | 100 |
| Composition 1 (first batch of doses) | (17 + 250) + 125 | 87 |
| | (33 + 500) + 250 | 92 |
| | (66 + 1000) + 500 | 98 |
| | (133 + 2000) + 1000 | 100 |

-continued

| Composition | Doses (mg/l) (fenamidone + fosetyl-Al + imazalil) | % Efficacy |
|---|---|---|
| Composition 2 (second batch of doses) | (10 + 150) + 75 | 78 |
| | (20 + 300) + 150 | 92 |
| | (40 + 600) + 300 | 94 |
| | (80 + 1200) + 600 | 100 |

The untreated control is 30% contaminated.

The above results show that:

the compositions according to the invention possess a preventive and curative activity compared with untreated controls.

the compositions according to the invention have a better efficacy compared with the known compositions, this being even at lower comparable product doses.

What is claimed is:

1. Fungicide compositions comprising:

a) fungicide compound of general formula (I):

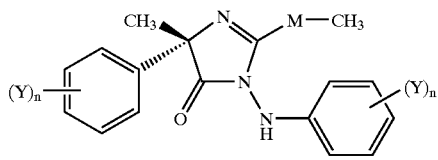

in which;

M represents an oxygen or sulphur atom;

n is an integer equal to 0 or 1;

Y is a fluorine or chlorine atom, or a methyl radical; and b) imazalil.

2. Method for treating fruits, characterized in that the fruits are treated with a fungicide composition according to claim 1, by immersion, spraying, brushing, coating or film-coating of the said fruits.

3. Method for treating fruits according to claim 2, characterized in that the dose of fenamidone is between 10 mg/l and 1000 mg/l.

4. Method for treating fruits according to claim 2, characterized in that the dose imazalil is between 100 mg/l and 3000 mg/l.

5. Method for treating fruits according to claim 2, characterized in that the said treatment is carried out after harvesting the fruits.

6. Method for treating fruits according to claim 2, characterized in that the fungicide compounds are applied simultaneously, sequentially or separately.

7. Method for treating fruits according to claim 2, characterized in that a) an additional fungicide different from said fungicide composition, or b) an insecticide, is applied to said fruits.

8. Fruits treated by the method of claim 2.

9. A method of treating fruit according to claim 2, characterized in that the dose of fungicidal compounds of general formula (I) is between 20 mg/l and 300 mg/l and the dose of imazalil is between 50 mg/l and 2500 mg/l.

10. Method for treating fruits according to claim 2, characterized in that the fruit is subject to attack by one or more phytopathogenic fungi selected from the group consisting of:

Phytophthora spp.;

Penicillium spp.;

bitter rot of citrus fruits (*Geotrichum candidum*);

black rot of citrus fruits (*Alternaria citri*);

anthracnose (*Colleotrichum gloeosporioides*); and melanose or phomopsis rot (*Diplodia natalensis* or *Phomopsis citri*).

11. Method for treating fruits according to claim 2, characterized in that the amount of the composition is that which protects or controls fungal attacks and prevents or stops the rotting of edible fruits.

12. Method for treating fruits according to claim 2, characterized in that the fruits are citrus fruits.

13. The fungicide compositions of claim 1 further comprising one or more additional fungicide compounds.

14. Fungicide compositions according to claim 13, characterized in that at least one additional fungicide compound is selected from the group consisting of phosphorous acid, its derivatives and its salts.

15. Fungicide compositions according to claim 13, characterized in that at least one additional fungicide compound is fosetyl-Al.

16. Fungicide compositions according to claim 13, characterized in that the additional fungicide compound or compounds is or are present at a dose of between 500 mg/l and 6000 mg/l.

17. Fungicide compositions according to claim 1, characterized in that they comprise, in addition to the fungicide compounds, one or more solid or liquid inert carriers, surfactants, protective colloids, adhesives, thickeners, thixotropic agents, penetrating agents, stabilizers, sequestrants, texturing agents, flavouring agents, taste enhancers, sugars, sweeteners and colorants.

18. Fungicide compositions according to claim 17, characterized in that they contain 0.05 to 95% by weight of said fungicide compounds.

19. Fungicide compositions according to claim 1, characterized in that they are in solid or liquid form.

20. Fungicide compositions useful for controlling phytopathogenic fungi investing or capable of infesting fruits comprising:

a) fenamidone, and b) imazalil.

21. Fungicide compositions according to claim 20, further comprising fosetyl-Al.

* * * * *